US00PP11283P

United States Patent [19]

VandenBerg

[11] Patent Number: Plant 11,283

[45] Date of Patent: Mar. 14, 2000

[54] CHRYSANTHEMUM PLANT NAMED 'YOBATON ROUGE'

[75] Inventor: Cornelis P. VandenBerg, Salinas, Calif.

[73] Assignee: Yoder Brothers, Inc., Barberton, Ohio

[21] Appl. No.: 09/112,537

[22] Filed: Jul. 9, 1998

[51] Int. Cl.[7] ..... A01H 5/00

[52] U.S. Cl. ..... Plt./286

[58] Field of Search ..... Plt./286, 298

[56] References Cited

U.S. PATENT DOCUMENTS

P.P. 10,251 2/1998 VandenBerg ..... Plt./286

*Primary Examiner*—Howard J. Locker

*Attorney, Agent, or Firm*—C. A. Whealy

[57] ABSTRACT

A distinct cultivar of Chrysanthemum plant named 'Yobaton Rouge', characterized by its compact and uniformly mounded plant habit; freely branching habit; uniform flowering; numerous inflorescences per plant; daisy-type inflorescences that are about 6.6 cm in diameter; bi-colored ray florets with bright red centers and yellow margins; bright yellow disc florets; early flowering; and excellent postproduction longevity with inflorescences and leaves maintaining good substance and color for about four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yobaton Rouge. The plant is being marketed under the name Baton Rouge.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in August, 1993, in Salinas, Calif., of the commercial Chrysanthemum cultivar Penny Lane (disclosed in U.S. Plant Pat. No. 6,238) as the male, or pollen, parent with an unnamed proprietary Chrysanthemum seedling selection, code number YB-6083, as the female, or seed, parent.

The new Chrysanthemum was discovered and selected by the inventor as a flowering plant within the progeny of the stated cross in a controlled environment in Salinas, Calif., in March, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yobaton Rouge has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yobaton Rouge'. These characteristics in combination distinguish 'Yobaton Rouge' as a new and distinct Chrysanthemum:

1. Compact and uniformly mounded plant habit.

2. Freely branching habit.

3. Uniform flowering.

4. Numerous inflorescences per plant.

5. Daisy spray-type inflorescences that are about 6.6 cm in diameter.

6. Bi-colored ray florets with bright red centers and yellow margins.

7. Bright yellow disc florets.

8. Early flowering.

9. Excellent postproduction longevity with inflorescences and leaves maintaining good substance and color for about four weeks in an interior environment.

The new Chrysanthemum is similar in ray floret color to the Chrysanthemum cultivar Mobile (disclosed in U.S. Plant Pat. No. 9,335). However in side-by-side comparisons in Salinas, Calif., and Leamington, Ontario, Canada, under commercial practice, plants of the new Chrysanthemum differed from plants of the cultivar Mobile in the following characteristics:

1. Plants of the new Chrysanthemum are more compact than plants of the cultivar Mobile.

2. Plants of the new Chrysanthemum are denser and less open than plants of the cultivar Mobile.

3. Plants of the new Chrysanthemum have smaller leaves, shorter petioles and smaller inflorescences than plants of the cultivar Mobile.

4. Plants of the new Chrysanthemum and the cultivar Mobile differ in leaf shape.

5. Plants of the new Chrysanthemum have a brighter red ray floret color than plants of the cultivar Mobile.

6. Ray florets of plants of the new Chrysanthemum have yellow longitudinal stripes along the margins whereas ray florets of plants of the cultivar Mobile are yellow at the base.

7. Inflorescences of plants of the cultivar Mobile have an inner row of feathered ray florets whereas plants of the new Chrysanthemum do not have an inner row of feathered ray florets.

A detailed comparison of plants of the new Chrysanthemum and the cultivar Mobile appears in Chart A at the end of the specification.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yobaton Rouge'.

The photograph at the bottom of the first sheet is a close-up view of typical inflorescences of plants of 'Yobaton Rouge'.

The photograph at the top of the second sheet is a close-up view of upper and lower surfaces of typical inflorescences (top) and typical leaves (bottom) of plants of 'Yobaton Rouge'.

The photograph at the bottom of the second sheet comprises a side perspective view of typical plants of 'Yobaton Rouge' (left) and 'Mobile' (right) showing the differences in plant size and shape, ray floret coloration, inflorescence size and presence of feathered inner ray florets on 'Mobile'. Floret and foliage colors in the photographs may appear different from the actual colors due to light reflectance.

DETAILED BOTANICAL DESCRIPTION

In the following description, color references are made to The *Royal Horticultural Society Colour Chart* except where general terms of ordinary dictionary significance are used. The following observations and measurements descibe plants grown in Leamington, Ontario, Canada, and Salinas, Calif., under greenhouse conditions which approximate those generally used in commercial potted Chrysanthemum production. Four unrooted cuttings were directly stuck in a 15—cm container and pinched once. Measurements and numerical values represent averages of typical flowering plants.

Botanical classification: *Dendranthema grandiflora* cultivar Yobaton Rouge.

Commerical classification: Daisy spray-type pot chryasanthemum.

Parentage:

*Male or pollen parent.*—*Dendranthema grandiflora* cultivar Penny Lane, disclosed in U.S. Plant Pat. No. 6,238.

*Female or seed parent.*—Unnamed proprietary *Dendranthema grandiflora* seedling selection, code number YB—6083.

Propagation.

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy spray-type pot Chrysanthemum. Inverted triangle. Stems initially upright, then somewhat spreading giving a uniformly mounded appearance to the plant. Freely branching; about four lateral branches develop after removal of terminal apex (pinching), dense and full plants.

*Plant height.*—Compact, about 20 cm.

*Plant width.*—About 35 cm.

*Foliage description.*—Arrangement: Alternate. Length: About 6.1 cm. Width: About 4.9 cm. Apex: Mucronate. Base: Truncate. Margin: Palmately lobed, sinuses between lateral lobes parallel. Texture: Upper and lower surfaces slightly pubescent. Veins prominent on lower surface. Petiole length: About 1.3 cm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Daisy spray-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about four weeks in an interior environment.

*Quantity of inflorescences.*—About eight inflorescences per terminal with about 32 inflorescences per plant.

*Inflorescence bud.*—Height: About 6 mm. Diameter: About 7 mm. Color: Close to 143A.

*Inflorescence size.*—Diameter: About 6.6 cm. Depth (height): About 1.2 cm. Diameter of disc: About 1.5 cm.

*Ray florets.*—Shape: Oblong with short corolla tube. Aspect: Straight, flat. Orientation: Slightly upright. Length: About 3.6 cm. Width: About 9 mm. Apex: Rounded. Margin: Entire. Texture: Smooth, glabrous, velvety. Number of ray florets per inflorescence: About 21. Color: When opening, upper surface: Red, 46A to 46B, center; yellow, 7A, margins and base. When opening, lower surface: Mostly yellow, close to 8A to 8B. Fully opened, upper surface: Red, 46A to 45A, center; yellow, close to 9A, margins, base and faint longitudinal streaks. Fully opened, lower surface: Mostly yellow, 7B; reddish, close to 45A, streaks.

*Disc florets.*—Shape: Tubular. Apex: Dentate. Length: About 5.5 mm. Width: Apex: About 2.5 mm. Base: About 1.5 mm. Number of disc florets per inflorescence: About 94. Color: Immature: 144A to 154A. Mature: Apex: Close to 9A. Mid-section and base: White, 155D.

*Peduncle.*—Aspect: Flexible, strong, angled about 50° to stem. Length: First peduncle: About 9 mm. Fourth peduncle: About 2.4 cm. Texture: Pubescent. Color: Darker than 144A.

*Reproductive organs.*—Androecium: Present on disc florets only. Anther color: 9A. Pollen: Amount: Moderate. Color: Close to 9A. Gynoecium: Present on both ray and disc florets.

Disease resistance: No known Chrysanthemum diseases observed to date on plants grown under commercial greenhouse conditions.

Seed production: Seed production has not been observed.

| CHARACTERISTIC | 'YOBATION ROUGE' | 'MOBILE' |
|---|---|---|
| PLANT HEIGHT | About 20 cm | About 29 cm |
| PLANT WIDTH | About 35 cm | About 42 cm |
| LEAF LENGTH | About 6.1 cm | About 8.5 cm |
| LEAF WIDTH | About 4.9 cm | About 6.4 cm |
| LEAF SINUSES | Parallel | Overlapping |
| LEAF BASE | Truncate | Attenuate |
| PETIOLE LENGTH | About 1.3 cm | About 2.4 cm |
| INFLORESCENCE DIAMETER | About 6.6 cm | About 7.4 cm |
| RAY FLORET LENGTH | About 3.6 cm | About 3.9 cm |
| RAY FLORET WIDTH | About 9 mm | About 1 cm |

-continued

| CHARACTERISTIC | 'YOBATION ROUGE' | 'MOBILE' |
|---|---|---|
| RAY FLORET APEX | Rounded | Dentate |
| RAY FLORET COLOR, UPPER SURFACE | Red, 46A/45A, center; Yellow, close to 9A, margins | Distal: 46A/179A, dulled Proximal: 9A |
| RAY FLORET COLOR, LOWER SURFACE | 7B; reddish, close to 45A, streaks | Distal: close to 178A Proximal: 7B |

It is claimed:

1. A new and distinct cultivar of Chrysanthemum plant named 'Yobaton Rouge', as illustrated and described.

* * * * *

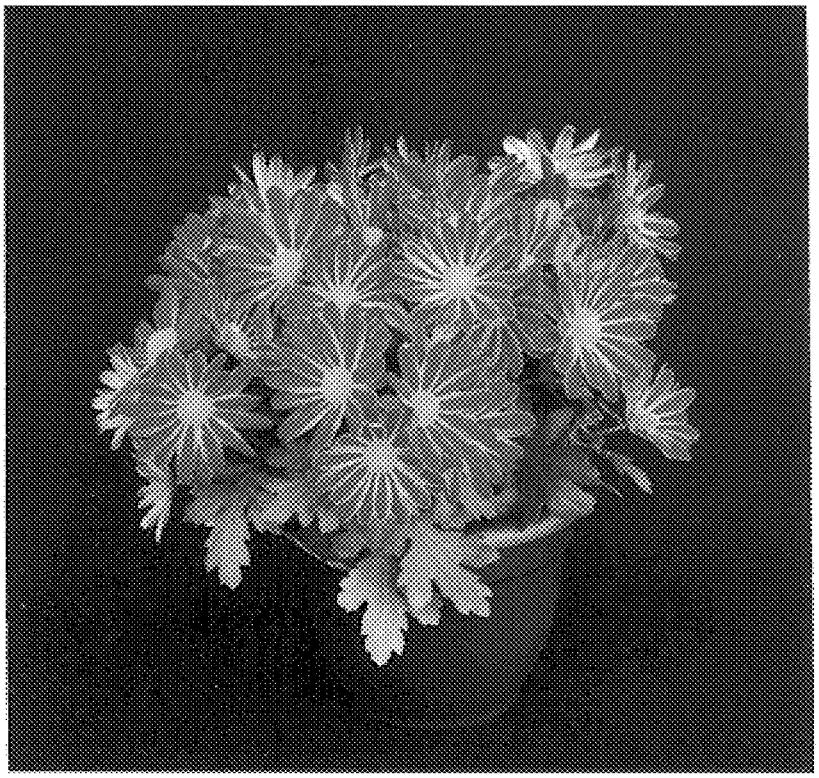
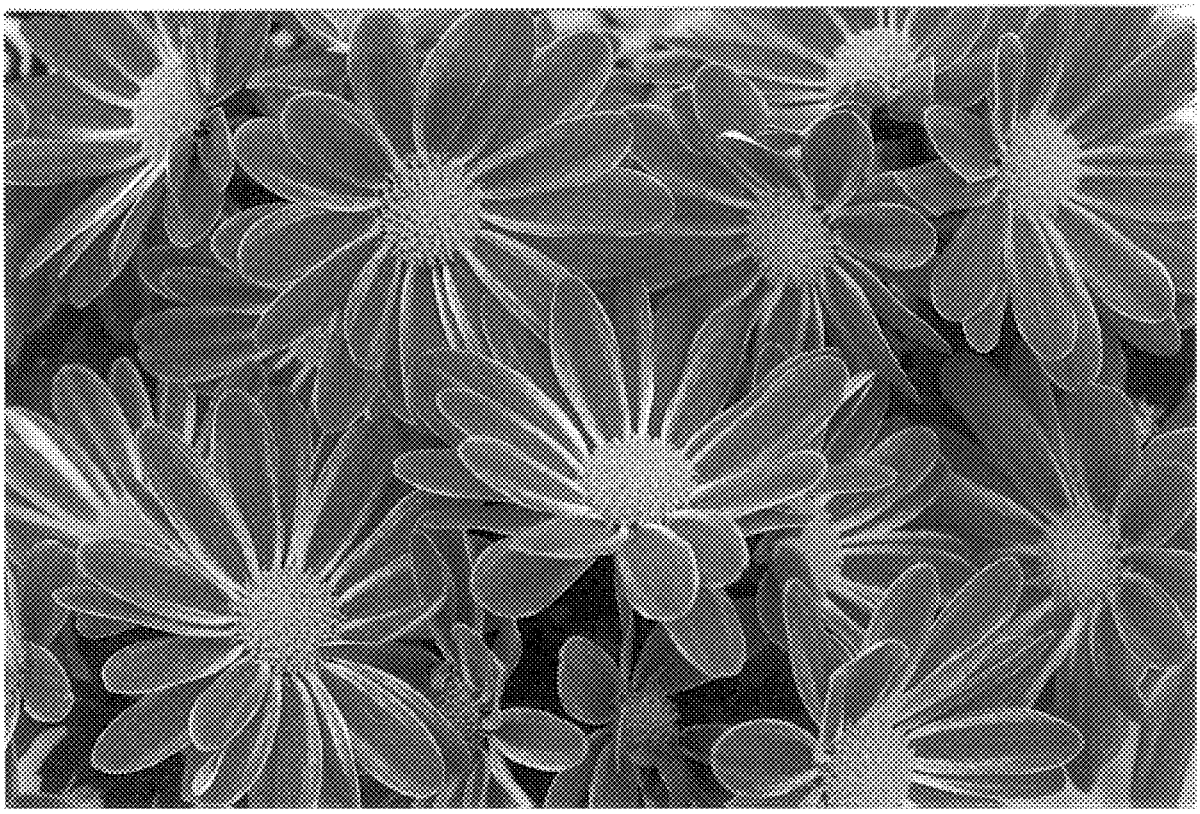

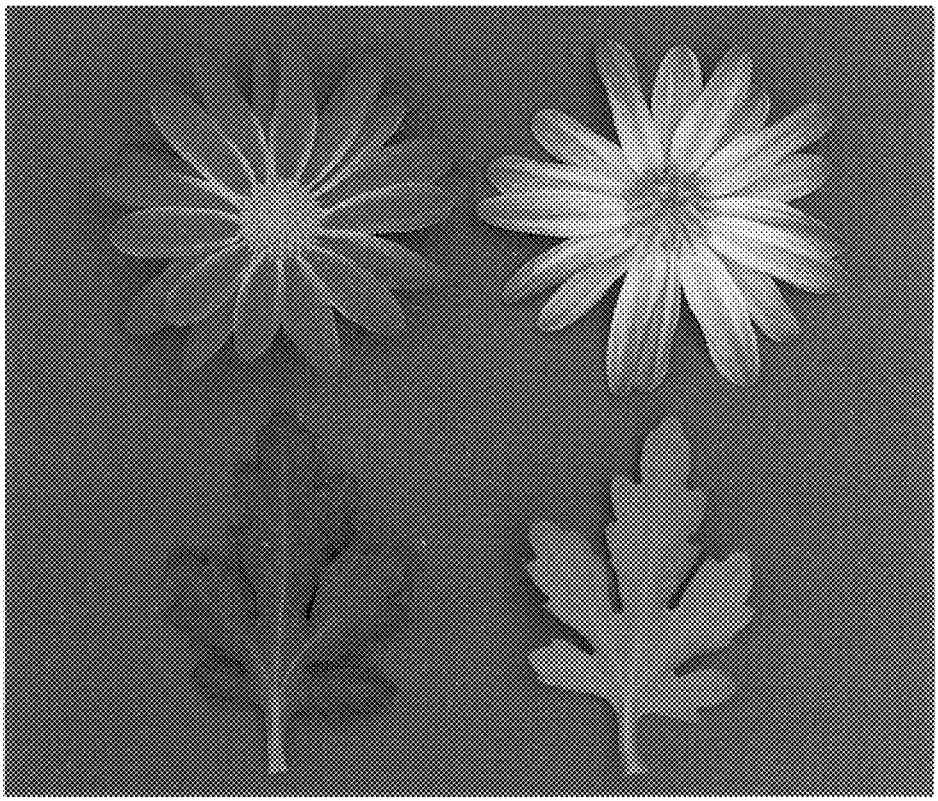
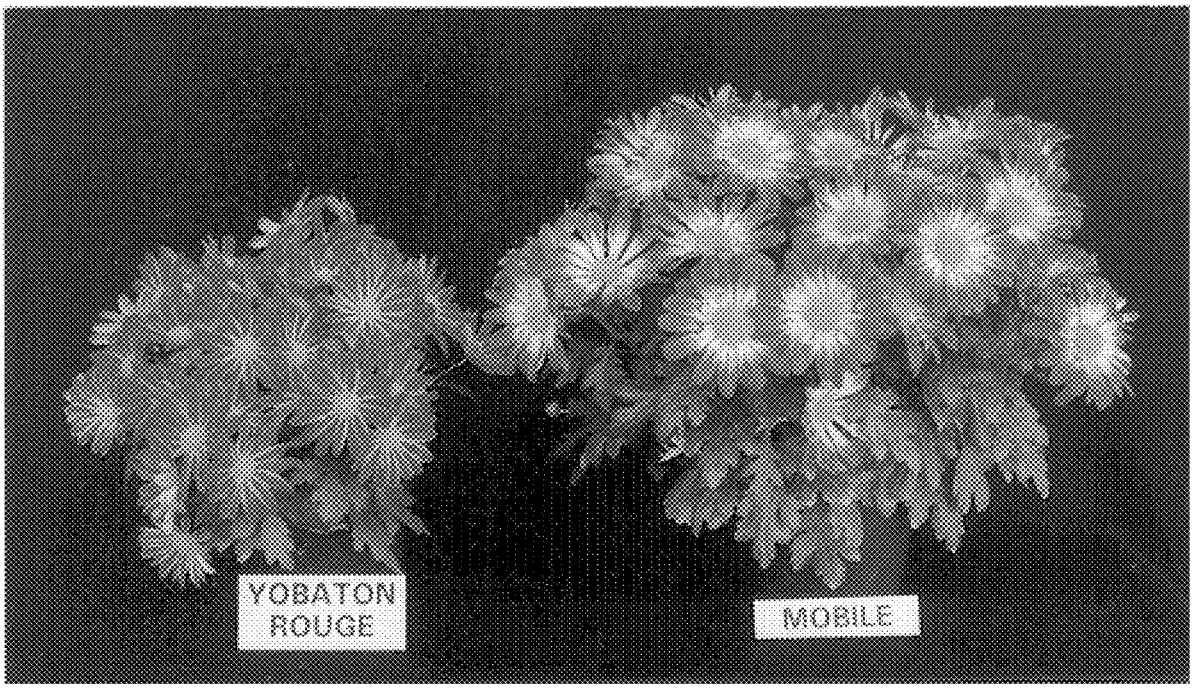
YOBATON
ROUGE
MOBILE